United States Patent
Adelman et al.

(10) Patent No.: US 7,022,688 B1
(45) Date of Patent: Apr. 4, 2006

(54) USE OF 17β-DIHYDROEQUILENIN AS AN ANTIOXIDANT

(75) Inventors: Steven J. Adelman, Doylestown, PA (US); Dorothy H. Prozialeck, Holland, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 08/985,667

(22) Filed: Dec. 5, 1997

Related U.S. Application Data

(60) Provisional application No. 60/032,656, filed on Dec. 10, 1996.

(51) Int. Cl.
*A61K 31/56* (2006.01)

(52) U.S. Cl. ...................................................... 514/182

(58) Field of Classification Search ................ 514/182, 514/385, 912
See application file for complete search history.

(56) References Cited

U.S. PATENT DOCUMENTS 4,154,820 A    5/1979   Simoons

FOREIGN PATENT DOCUMENTS

| EP | 0744176 | 11/1996 |
|----|---------|---------|
| EP | 0761679 | 3/1997  |
| WO | 9409789 | 5/1994  |

OTHER PUBLICATIONS

Bhavnani, B.R. et al., Interaction of ring B unsaturated estrogens with estrogen receptors of human endometrium and rat uterus, Steroids, vol. 56, Apr. 1991, p. 201.

Stern, M.D. et al., Studies on the mechanism of action of conjugated equine oestrogens, Endometrial Cancer, (1978), p. 309.

Stern, M.D., Pharmacology of conjugated oestrogens, Maturitas, (1982) pp. 333-339.

Weisiger, R.A., Oxygen radicals and Ischemic Tissue Injury, Gastroenterology, vol. 90, No. 2, p. 494.

Biemond, P. et al., Superoxide dependent iron release from ferritin in inflammatory diseases, Free Radical Biology and Medicine, vol. 4, (1988) pp. 185-198.

Braughler, J.M. et al., Central nervous system trauma and stroke, Free Radical Biology and Medicine, vol. 6, (1989) pp. 289-301.

Rice-Evans, C.A. et al., Current Status of antioxidant therapy, Free Radical Biology and Medicine, vol. 15 (1993) pp. 77-96.

Del Maestro, R.F., An approach to free radicals in medicine and biology, Acta Physiol. Scand, (1980) Suppl. 492:153-168.

Subbiah, M.T.R. et al., Antioxidant potential of specific estrogens on lipid peroxidation J. Clin. Endocr. Metab., 1993, 77:1095-7.

Wiseman, H., Tamoxifen: new membrane-mediated mechanisms of action and therapeutic advances, TIPS, vol. 15 (Mar. 1994).

Tang, M. et al., Metab Clin Exp, 1996, 45(4), pp. 411-414.

*Primary Examiner*—Zohreh Fay
(74) *Attorney, Agent, or Firm*—Arnold S. Milowsky, Esq.; Cozen O'Connor

(57) ABSTRACT

This invention provides a method of using 17β-dihydroequilenin or a pharmaceutically acceptable salt of 17β-dihydroequilenin-3-sulfate ester as an antioxidant.

2 Claims, No Drawings

USE OF 17β-DIHYDROEQUILENIN AS AN ANTIOXIDANT

BACKGROUND OF THE INVENTION

This application claims the benefit of U.S. Provisional Application No. 60032,656, filed Dec. 10, 1996.

Biologically generated free radicals have been implicated in a large number of disease states. The survival of aerobic organisms in an oxygen environment involves a complicated interplay between the biological generation of these very reactive chemical species and the ability of the organism to control them (Del Maestro RF, Acta Phy Scan Suppl. 492: 153–68 (1980)). This interplay between the host organism and biologically generated free radicals results in profound biochemical alterations which culminate in cellular injury and death of the organism. The accumulated products of free radical reactions result in some of the large number of disease conditions which have been suggested to result, in part, from cellular injury induced by an increased flux of intracellular free radicals. These include, but are not limited to cancers, cardiovascular disease, central nervous system disorders, bone disease, aging, Alzheimer's dementia, inflammatory disorders, rheumatoid arthritis, autoimmune diseases, respiratory distress and emphysema.

The association of free radical damage with many disease states is well documented and many cellular constituents, including enzymes, ion channels, structural proteins and membrane lipids are potential targets for reactive free radical species (Rice-Evans C, Mol Aspects of Med 13(1):1–111 (1992)). The antioxidant status at the appropriate site will limit the damage. Free radical reaction with these potential targets may compromise a range of cellular functions leading to pathological change and ultimately cell death. The antioxidant status at the potential reaction site will limit damage. Antioxidants play an important role in protecting DNA, proteins (including lipoproteins) and membrane lipids against oxidative damage.

There is strong evidence that free radical damage contributes to the etiology of many chronic health problems. For most human diseases, oxidant formation from endogenous sources is secondary to the initial disease process, but oxidative damage exacerbates the primary lesion. For example, reperfusion injury can be defined as the damage that occurs to an organ during the resumption of blood flow following an episode of ischaemia. Oxygen restoration, although necessary, causes increased oxidant formation in the damaged tissue and temporarily worsens the injury (Uraizee A, Circulation 75(6):1237–1248 (1987)). The decline in the antioxidant defenses in the hypoxic myocardium followed by an increase in lipid peroxidation upon reoxygenation was documented by Guanieri (Biochim-Biophys-ACTA 718(2):157–164 (1982)). In reperfusion injury, the inflammatory response at the site of injury on the endothelium after the ischemic insult generates superoxide from adhesion and activation of neutrophils. In a number of different clinical conditions, the production of oxygen free radicals in the liver is also increased. In viral hepatitis and in chronic active hepatitis, a high number of stimulated macrophages accumulate in the liver, and they produce free radicals. A large number of toxic chemicals cause toxic liver injury, due to increased free radical generation in the liver, frequently mediated by the cytochrome P-450. It can be concluded that hydroxyl radical formation catalyzed by iron released from ferritin is a mechanism incidental to many liver diseases (Lee W M, N Eng J of Med Review P.1118 (1995)).

Oxidation and the use of antioxidants is also important for the treatment of numerous inflammatory disease states. Rheumatoid arthritis (RA) is the most common chronic inflammatory disease. Epidemiological studies reveal a prevalence rate of classical and definite RA between 0.3 and 1.5 percent. Joint disease with chronic persistent inflammation is accompanied by the formation of $H_2O_2$ in the inflamed rheumatoid joint. During inflammation, oxygen free radicals are also produced, especially by polymorphonuclear leukocytes (PMN) and macrophages. In any chronic or acute inflammatory disease, PMN and macrophages will produce both $O_2$- and $H_2O_2$. Tuberculosis, psoriasis, systemic lupus erythematosus, other autoimmune diseases, and adult respiratory distress syndrome can also be mentioned as inflammatory diseases with oxidation as a contributor, and many others can be added to this list.

The generation of oxygen radicals and the process of lipid peroxidation have also become a focus of attention for investigators in the fields of central nervous system (CNS) trauma and stroke (e.g., ischemia). Numerous studies have provided considerable support for the occurrence of free radical and lipid peroxidation reactions in the injured or ischemic CNS (Hall ED, J-Neurotrauma 9(Suppl. 1):S165–S172 (1992)).

Antioxidants have been suggested to be protective against breast cancer and other cancers including those of the brain and liver, as well as to protect against cardiovascular disease and osteoporosis (Wiseman H, Free Radical Res 21(3): 187–94 (1994)). They have been demonstrated to protect model and cellular membranes including the nuclear membrane against potentially carcinogenic free radical intermediates and the products of lipid peroxidation. Severe complications associated with atherosclerosis and its common incidence have focused attention on prevention and therapy of this vascular disease state, possibly through their ability to protect low density lipoproteins (LDL) against oxidative damage (Steinberg D, N Engl J of Med 14:915–924 (1989)).

DESCRIPTION OF THE INVENTION

In accordance with this invention, there is provided a method of treating or inhibiting free radical induced disease states by administering an antioxidant amount of 17β-dihydroequilenin or its pharmaceutically acceptable salt of the 3-sulfate ester, to a mammal in need thereof. As a corollary of that process, this invention provides a process for treating free radical reactions with enzymes, ion channels, structural proteins and membrane lipids in a mammal, which comprises administering 17β-dihydroequilenin or a pharmaceutically acceptable sulfate ester salt thereof, as a sacrificial substrate, in an amount sufficient to selectively react with and inhibit free radical reaction with the patients enzymes, ion channels, structural proteins or membrane lipids. Specific situations in which antioxidant therapy is indicated to be warranted are with cancers, central nervous system disorders, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke.

As used in accordance with this invention, treating covers treatment of an existing condition, ameliorating the condition, or providing palliation of the condition and inhibiting includes inhibiting or preventing the progress or development of the condition.

Pharmaceutically acceptable salts of 17β-dihydroequilenin 3-sulfate ester include, but are not limited to, the alkli metal salts, alkaline earth metal salts, ammonium salts, alkylamine salts containing 1–6 carbon atoms or dialkylamine salts containing 1–6 carbon atoms in each alkyl group.

The antioxidant properties of 17β-dihydroequilenin were established in a standard pharmacological test procedure that measured the its ability to inhibit the formation of oxidatively modified low density lipoprotein (LDL) induced by exposure to either Cu++ ions or cultured endothelial cells (Parthasarathy S, Proc Natl Acad Sci USA 86:1046–1050 (1989)) by the TBARS (thiobarbituric acid reactive substances) method for analysis of free aldehydes (Yagi K., Biochem Med 15:212–216 (1976)).

The results obtained in this standard pharmacological test procedure demonstrate that 17β-dihydroequilenin is a potent inhibitor of LDL oxidation, inhibiting the process by up to 100%. An $IC_{50}$ of 0.315 μM was obtained in the pocine aortic endothelial cell mediated oxidation assay. By comparison, an $IC_{50}$ of 0.56 μM was obtained for estrone in this test procedure.

Based on the results obtained in these test procedures, 17β-dihydroequilenin and the pharmaceutically acceptable salts of its sulfate ester, such as the alkali metal salts, alkaline earth metal salts, ammonium salts, alkylamine salts containing 1–6 carbon atoms, or dialkylamine salts containing 1–6 carbon atoms in each alkyl group, are therefore useful as antioxidants, and in the treatment or inhibition of free radical induced disease states.

The antioxidants of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The antioxidants of this invention may be administered rectally in the form of a conventional suppository. For administration by intranasal or intrabronchial inhalation or insufflation, the antioxidants of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the antioxidants of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.02 μg/kg –500 μg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A method of inhibiting or treating free radical induced disease states selected from the group consisting of emphysema, viral hepatitis, tuberculosis, psoriasis, systemic lupus erythematosus, by administering an antioxidant amount of 17β-dihydroequilenin or a pharmaceutically acceptable salt of 17β-dihydroequilenin-3-sulfate ester, to a mammal in need thereof.

2. The method of claim 1 wherein the pharmaceutically acceptable salt of the 3-sulfate ester is an alkali metal salt, alkaline earth metal salt, ammonium salt, alkylamine salt containing 1–6 carbon atoms, or dialkylamine salt containing 1–6 carbon atoms in each alkyl group.

* * * * *